Figure 1:
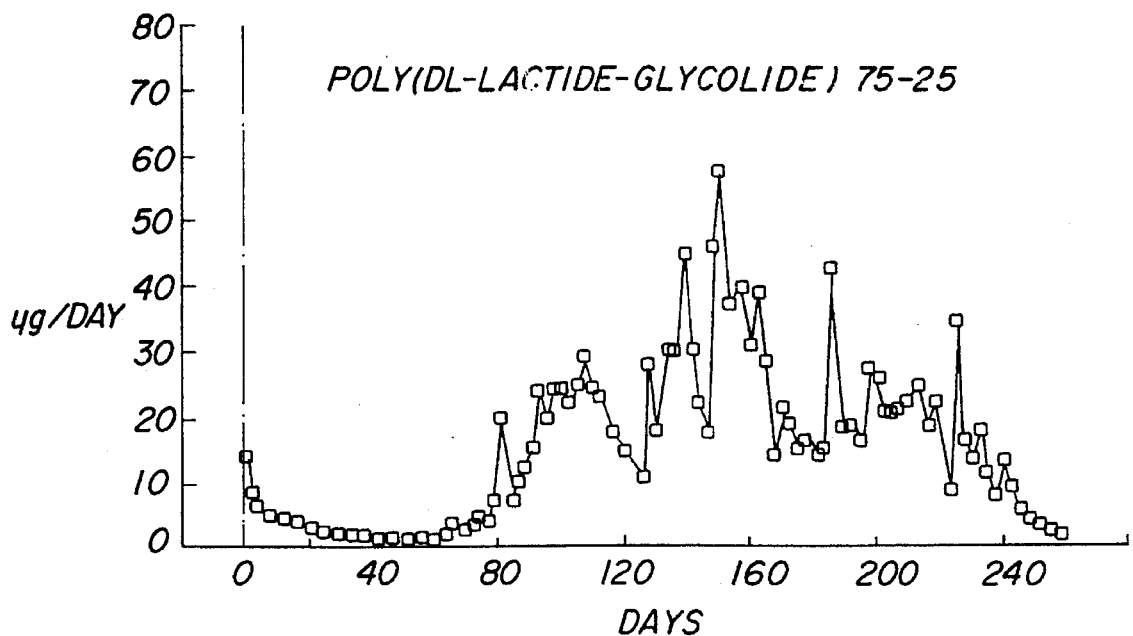

United States Patent [19]

Billot et al.

[11] Patent Number: 5,540,937
[45] Date of Patent: Jul. 30, 1996

[54] PROCESS FOR PREPARING MICROSPHERES FOR THE PROLONGED RELEASE OF THE LHRH HORMONE AND ITS ANALOGUES, MICROSPHERES AND FORMULATIONS OBTAINED

[75] Inventors: Geneviève B. Billot, Lyons; Marc M. Teichner, Sainte Foy Les Lyon, both of France

[73] Assignee: Rhone Merieux, Lyons, France

[21] Appl. No.: 97,014

[22] Filed: Jul. 27, 1993

[30] Foreign Application Priority Data

Jul. 27, 1992 [FR] France ................................. 92 09241

[51] Int. Cl.$^6$ ............................... A61K 9/14; A61K 9/50
[52] U.S. Cl. ............................................ 424/489; 424/501
[58] Field of Search ......................................... 424/489, 501

[56] References Cited

U.S. PATENT DOCUMENTS

| | | |
|---|---|---|
| 3,523,906 | 8/1970 | Vrancken et al. . |
| 3,691,090 | 9/1972 | Kitajima et al. . |
| 3,737,337 | 6/1973 | Schnoring et al. . |
| 3,773,919 | 11/1973 | Boswell et al. . |
| 3,887,699 | 6/1975 | Yolles . |
| 3,891,570 | 6/1975 | Fukushima et al. . |
| 3,960,757 | 6/1976 | Morishita et al. . |
| 4,389,330 | 6/1983 | Tice et al. ................................. 424/38 |
| 4,530,840 | 7/1985 | Tice et al. . |
| 4,542,025 | 9/1985 | Tice et al. . |
| 4,673,595 | 6/1987 | Orsolini et al. . |
| 4,675,189 | 6/1987 | Kent et al. . |
| 4,818,542 | 4/1989 | Deluca et al. . |
| 4,835,139 | 5/1989 | Tice et al. . |
| 4,897,268 | 1/1990 | Tice et al. . |
| 4,935,245 | 6/1990 | Horn et al. ............................. 424/501 |
| 5,100,669 | 3/1992 | Hyan et al. . |
| 5,192,741 | 3/1993 | Orsolini et al. . |

FOREIGN PATENT DOCUMENTS

| | | |
|---|---|---|
| 058481 | 8/1982 | European Pat. Off. . |
| 145240 | 11/1984 | European Pat. Off. . |
| 251476 | 1/1988 | European Pat. Off. . |
| 281482 | 9/1988 | European Pat. Off. . |
| 315875 | 5/1989 | European Pat. Off. . |
| 442671 | 8/1991 | European Pat. Off. . |
| 467389 | 1/1992 | European Pat. Off. . |
| 91/13595 | 9/1991 | WIPO . |
| 9112882 | 9/1991 | WIPO . |

OTHER PUBLICATIONS

Bodmeier et al, "The preparation and evaluation of drug--containing . . . ", Pharmaceutical Research, vol. 4, No. 6, 1987, pp. 465–471.

Bodmeier et al, "Polylactic acid microspheres containing quinidine . . . ", J. Microencapsulation, 1987, vol. 4, No. 4, pp. 289–297.

Ogawa et al, "A new technique to efficiently entrap leuprolide acetate . . . ", Chem Pharm Bull, No. 3, pp. 1095–1103.

Heya et al, "Effects of counteranion of TRH and loading amount . . . ", International Journal of Pharmaceutics, vol. 69, 1991 pp. 69–75.

(List continued on next page.)

*Primary Examiner*—Nathan M. Nutter
*Assistant Examiner*—John M. Cooney, Jr.
*Attorney, Agent, or Firm*—Larson & Taylor

[57] ABSTRACT

Process for preparing microspheres for the prolonged release of the LHRH hormone and of its analogues, the hormone being dispersed in a water-insoluble polymer or copolymer matrix, the solvent evaporation process is characterized by the use of a pair of organic solvents of which one makes it possible more specifically to obtain a homogeneous suspension of the hormone in the pulverulent state by simply stirring and of which the other is slightly water-miscible so as to allow more specifically the microdispersion of the organic phase in the aqueous phase in which the hardening of the microspheres is performed. This process leads to the preparation of LHRH-containing microspheres which are noteworthy for their purity, especially to microspheres with complex matrices, as well as to formulations comprising at least two types of microspheres.

20 Claims, 3 Drawing Sheets

OTHER PUBLICATIONS

Bodmer et al, "Sustained release of the somatostatin analogue . . . ", Proceed. Intern. Symp. Control. Rel. Bioact. Mater., vol. 18, 1991, pp. 597–598.

Chang, "Biodegradable semipermeable microcapsules containig enzymes . . . ", Journal of Bioengineering, vol. 1, 1976, pp. 25–32.

Tice et al, "3–month and 6–month delivery of peptides (LHRH) from . . . ", Proceed. Intern. Symp. Control. Rel. Bioact. Mater., vol. 18, 1991, pp. 467–468.

Burns et al, "Nafarelin controlled release injectible: theoretical . . . ", J. Microencapsulation, 1990, vol. 7, No. 3, pp. 397–413.

Cowsar et al, "Poly(lactide–co–glycolide) microcapsules for controlled release of steroids", Methods in Enzymology, vol. 112, 1985, pp. E82–E97.

PROCESS FOR PREPARING MICROSPHERES FOR THE PROLONGED RELEASE OF THE LHRH HORMONE AND ITS ANALOGUES, MICROSPHERES AND FORMULATIONS OBTAINED

The invention relates to the preparation of injectable microspheres for the prolonged release of the LHRH hormone or of its analogues. The preparation of these microspheres involves biodegradable and biocompatible polymers or copolymers in which the polypeptide is dispersed. The invention also relates to prolonged-release microspheres and formulations capable of being obtained by this process.

Microspheres are understood to mean particles in which the polypeptide is dispersed in the polymer matrix. These particles are injectable in animals or in man after suspension in a suitable liquid.

The biodegradable and biocompatible polymers used are generally poly(DL-lactide-glycolide-) produced by polymerization by ring opening, poly(lactic glycolic acids) produced by polycondensation of lactic acid with glycolic acid, polycaprolactones and copolymers, polyacetals, polyorthoesters, polyhydroxybutyrates and copolymers.

Numerous methods for the microencapsulation of water-soluble polypeptides into biodegradable polymers have been described. These methods can be classified essentially into three groups:

coacervation or emulsion/phase separation technique,
encapsulation by spray-drying, and
solvent evaporation in organic or aqueous phase.

The coacervation or emulsion/phase separation technique (U.S. Pat. No. 4,675,189, U.S. Pat. No. 4,835,139; European Patent Application EP-A-0,302,582) occurs in organic phase. The peptide is dispersed in aqueous solution or in pulverulent form in an organic solution of the polymer. A phase inducer, generally a silicone oil, is added to the organic phase in order to induce coacervation of the polymer in the form of droplets of coacervate coating the polypeptide. These droplets fuse with one another to give embryonic microspheres. These microspheres are then transferred into a non-solvent of the polymer in order to induce their hardening. Since the polypeptides used are generally insoluble in the organic solvents and the oils used, the fraction encapsulated in the polymer is high.

However, this method has the disadvantage of consuming large quantities of solvents (dichloromethane, heptane or trichloro-trifluoro-ethane) and of oil. This results in high production costs and the need to guard against the toxic effects of the solvents and risks of ignition in the case of heptane. The coacervation step is, in addition, difficult to control: the production of individualized microspheres depends on the quantities of polymer, solvent and phase inducer in the mixture. Small excesses of phase inducer result in the partial or total aggregation of the microspheres, rendering the product obtained unusable. Moreover, the kinetics of release of the polypeptide encapsulated in a physiological medium is characterized by a large quantity released during the first few hours. This property may cause problematic side effects in vivo when the product is used for curative purposes, or may correspond to a loss of active ingredient.

The technique of encapsulation by spray-drying described for example in Patent Application EP-A-0,315,875 consists in preparing an emulsion of the peptide in aqueous solution in a mixture of polymers in organic solution, then in spraying this emulsion in a stream of hot air. Microspheres are obtained following the evaporation of the solvents during the spraying.

The basic technique of solvent evaporation consists in dispersing a polymer solution containing an active ingredient in a second solvent immiscible with that of the polymer, and then in evaporating the solvent for the polymer. A technique which is particularly used with the abovementioned polymers is the technique of evaporation of solvent in aqueous phase: a solution of the polymer, containing the active ingredient, is dispersed in a stirred aqueous solution. The solvent for the polymer is gradually removed by diffusion into the aqueous phase followed by evaporation at the surface of the mixture. The microspheres thus solidified can then be filtered and recovered. This technique is particularly used when the active ingredient which it is desired to encapsulate is insoluble in the aqueous phase. This technique is for example used successfully for the encapsulation and prolonged release of steroids (T. Tice, L. R. Beck, in: Dr. Mishell Jr. Editor, Long Acting Steroid Contraception, Raven Press, New York, 1983, 175–199).

U.S. Pat. No. 4,389,330 describes for example a process for preparing microcapsules in which the substance to be encapsulated is dissolved or dispersed in a solvent which is not very miscible with water, the wall-forming material is dissolved therein, the organic phase obtained is dispersed in a continuous-phase treatment medium which may be water or an organic liquid such as xylene, toluene and the like, then a portion of the solvent is evaporated before recovering the microcapsules and extracting the rest of the solvent which they contain. This process is used in this application only for water-insoluble substances, progesterone and norgestimate, which are dissolved in methylene chloride as solvent and then dispersed in an aqueous phase containing 5% PVA (polyvinyl alcohol). No distinction is made between the very different types of continuous-phase treatment media and the different solvents, for example THF and methylene chloride which may, nevertheless, behave very differently.

On the other hand, the technique of solvent evaporation by dispersion of an organic phase in an aqueous phase gives low encapsulation yields when the active ingredient is water-soluble. In this case, the active ingredient dissolved or dispersed in the organic solution may rapidly diffuse and dissolve in the aqueous phase (Bodmeier R., Mc Ginity J. W., Pharm. Res., 1987, 4, 465). The microspheres thus produced contain only a small proportion of initial active ingredient: most of the active ingredient is lost through dissolution in the aqueous phase.

The disadvantages of the conventional technique of solvent evaporation have led the specialist to find and develop, for the encapsulation of water-soluble substances, evermore complex and expensive techniques (coacervation: EP-A-0,302,582; U.S. Pat. No. 4,675,189; U.S. Pat. No. 4,835,139; spray-drying; double emulsion: EP-A-0,145,240; EP-A-0,442,671) or to adapt the solvent evaporation to special cases of water-soluble products.

In the case where the solubility of the active ingredient depends on the pH, an adjustment of the pH of the aqueous phase to a value corresponding to a low solubility of the active ingredient may make it possible to limit the partition of the active ingredient into the aqueous phase. However, this adjustment may be problematical when the pH of the aqueous phase needs to be adjusted to extreme values. Under these conditions, the active ingredient and the polymer may be unstable.

Another method used to limit the partition of the active ingredient into the aqueous phase consists in previously saturating the aqueous phase with the active ingredient so as to suppress or reverse the phenomenon (R. Bodmeier J. W., Mc Ginity, J. Microencapsulation, 1987, Vol. 4, no. 4, 289–297). The latter solution remains, however, unusable for the encapsulation of expensive water-soluble peptides or polypeptides since the necessary quantities of active ingredient which should be used in order to saturate the aqueous phase are too high.

A variant of the technique of encapsulation by solvent evaporation has been developed for the encapsulation of water-soluble peptides analogous to LHRH in poly(lactic-glycolic acids) produced by polycondensation (European Patent Application EO-A-0,145,240, Chem. Pharm. Bull. 36 (3), 1095–1103, 1988), for the encapsulation of TRH (Int. J. Pharm., 1991, 69, 69–75), the encapsulation of somatostatin in poly(DL-lactide-glycolide) branched on D.glucose (Proceed. Intern. Symp. Control. Rel. Bioact. Mater. 18, 1991, 597–598), the encapsulation of bovine albumin and horseradish peroxidase (Pharm. Research, vol. 8, no. 6, 713–720, 1991). This variant consists in forming a first emulsion of the water/oil type in which the active ingredient in solution in water is emulsified in the polymer in solution in an organic solvent, generally dichloromethane. The aqueous phase of this first emulsion may also contain a water-soluble additive which has the effect of increasing its viscosity. The increase in viscosity may be due either to a water-soluble macromolecular compound such as gelatine (EP-A-0,145,240), or to the ionic interaction existing between the peptide and the polymer (Int. J. Pharm., 1991, 69, 69–75).

This first emulsion is then dispersed in an aqueous phase containing a dispersion stabilizer so as to give an emulsion of the water/oil/water type. The solvent of the organic phase is evaporated under vacuum so as to induce the hardening of the microspheres. The microspheres are then harvested by centrifugation or filtration.

The fraction of peptide or polypeptide effectively encapsulated by this method is generally high.

The kinetics of release of the active ingredient largely depends on the encapsulation conditions, essentially the quantity of water, of active ingredient and of additive in the aqueous phase of the first solution, relative to the quantity of polymer and solvent in the organic phase. The production of this first emulsion is difficult in the case of the LHRH analogue (EP-A-0,145,240) since it involves the emulsification of the aqueous phase in the organic phase at high temperature, hence the need to carry out the procedure at a pressure greater than atmospheric pressure in order to avoid boiling and evaporation of this solvent. Moreover, the high temperature (69° to 70° C.) used during the formation of the first emulsion cannot be used for thermally unstable active ingredients.

Another variant of the technique of solvent evaporation consists in carrying out the dispersion of an organic phase in another immiscible organic phase. This variant theoretically makes it possible to limit the partition of a water-soluble active ingredient of the dispersed phase into the continuous phase. This technique of dispersion-evaporation of oil/oil solvent consists in dispersing, with stirring, an organic solution of the polymer containing the active ingredient in an inorganic oil or a second organic solvent immiscible with the solvent for the polymer. The polymer is for example dissolved in acetone or acetonitrile and then the solution obtained is dispersed in paraffin oil. Other solvent pairs have been described such as for example the pair hexafluoroacetone/carbon tetrachloride. However, the use of toxic solvents or of large quantities of paraffin oil limit the scope of this process.

Furthermore, for the preparation of microspheres comprising, dispersed in a polymer matrix, a water-soluble substance such as an enzyme, U.S. Pat. No. 3,691,090 proposes for its part, dispersing the substance in an organic solvent which is miscible or nearly miscible with water and in which the polymer is dissolved, and then suspending this organic phase in an aqueous solution comprising an inorganic salt which prevents the solubilization of the solvent so as to allow the phase separation.

In U.S. Pat. No. 3,737,337, the process proposes dispersing a substance, which is soluble or insoluble in water, in a solution of an organic solvent soluble in an amount of at most 15% by weight in water at 20° C., and then dispersing the organic phase obtained in an aqueous phase saturated with organic solvent or with salts so as to prevent, in a first instance, the solubilization of the solvent, and then gradually inducing the partition of the solvent from the organic phase to the aqueous phase by gradual addition of water.

Finally, International Patent Application WO 91/12882 adequately summarizes the state of the art regarding encapsulation of water-soluble peptides: the technique by solvent evaporation is traditionally recognized as being unsuitable for the latter; the method by coacervation is recognized as being the most suitable method.

This international application proposes, however, adapting the evaporation of solvent or emulsion/evaporation by choosing a new route which consists in solubilising the water-soluble peptide in a third solvent optionally supplemented with water and used jointly with the usual solvent such as dichloromethane. The third solvent is water-miscible. When the organic phase is dispersed in the aqueous phase, the dichloromethane is evaporated while the third solvent passes into the aqueous phase. While the encapsulation yield can exceed 90% in the case of some peptide substances such as salmon calcitonin, TPA (Tissue Plasminogen Activator) and insulin, the yields observed for the encapsulation of the LHRH hormone are of the order of 75%. These results reflect a non-negligible partition of the LHRH hormone with the third solvent.

Another major disadvantage of this process lies in the use of even large volumes of solvents which are difficult to extract, thereby resulting in a residual solvent level which may nevertheless reach 1.5% of the weight of the microsphere. Furthermore, especially when dichloromethane is used, a third solvent, such as ethanol, should be added to the aqueous phase in a quantity which may be as high as 20% by volume.

The object of the present invention is to provide a simple process for encapsulating the LHRH hormone and its analogues with satisfactory yields, especially greater than 80% and more particularly greater than 90%, and requiring low volumes of solvents for the production of microspheres with low levels of residues.

Another object of the invention is to propose a process which makes it possible to obtain microspheres for the prolonged release of LHRH or of its analogues over a period which may range from a few days to about 1 year when they are injected into a subject or placed in vitro in a physiological buffer.

The subject of the invention is therefore a process for preparing microspheres for the prolonged release of the LHRH hormone and of its analogues, the hormone being dispersed in a water-insoluble polymer or copolymer matrix, in which process the hormone is dispersed and the material intended to form the matrix is dissolved in an organic solvent, the organic phase thus obtained is suspended in a continuous aqueous phase, the organic solvent is evaporated and the microspheres formed are recovered, characterized in that the hormone is dispersed in the pulverulent state in a pair of organic solvents of which one, called dispersion solvent, makes it possible more specifically to obtain a homogeneous suspension of the hormone in the pulverulent state by simply stirring and of which the other, called second solvent, is slightly water-miscible so as to allow more specifically the microdispersion of the organic phase in the aqueous phase. It is noteworthy that the slightly water-miscible solvent decreases the partition of the hormone, which appears to be due especially to an onset of superficial hardening of the matrix following the leakage of this solvent.

LHRH hormone (Luteinizing Hormone Releasing Hormone, also called GnRH for gonadotropin-releasing hormone), is understood to mean the natural or synthetic hormone of human or animal origin. LHRH analogues are understood to mean especially the fragments, agonists and antagonists of LHRH and their salts. In the claims and the corresponding parts of the description, when reference is made to the hormone (or LHRH hormone) generally, it should of course be understood to mean the hormone itself as defined above, but also its analogues.

Very advantageously, this process uses small quantities of solvents compared to conventional processes for the encapsulation of water-soluble peptides. It makes it possible, in addition, to obtain a very good dispersion of the hormone and of its analogues without requiring the vigorous stirring techniques normally used. In addition, it avoids the use of large quantities of additional substances which may be present to a greater or lesser degree in the microspheres, such as gelatine, silicone oil, organic or inorganic salts, as well as the use of organic solvents having toxic properties, such as heptane, which are undesirable both as unintentional constituents of the microspheres and as residues from the process.

The viscosity of the organic phase is also an important parameter and it is preferred that it is between 0.01 and 10 Pa.s, preferably between 0.01 and 1 Pa.s, and especially greater than about 0.04 Pa.s.

According to a first embodiment of the process, the material intended to form the matrix is dissolved in the dispersion solvent where the hormone is then dispersed with stirring, the dispersion solvent is completely or partially, preferably completely, evaporated, the remainder is taken up with the second solvent and the organic phase is suspended in the aqueous phase.

According to a second embodiment of the process, the hormone is dispersed in a first instance in the dispersion solvent while the material intended to form the matrix is dissolved in the second solvent, then the two phases obtained are mixed in order to obtain the organic phase which is suspended in the aqueous phase.

The dispersion solvent is selected preferably from the solvents tetrahydrofuran (THF), acetone, dichloromethane, chloroform, toluene, methyl ethyl ketone, pyridine, benzyl alcohol, acetonitrile, ethyl acetate, dioxane, mixtures thereof, or alternatively chlorofluorocarbon-containing solvents, whereas the second solvent is advantageously dichloromethane or alternatively chloroform.

In advantageous cases, a single solvent can ensure the satisfactory implementation of the process according to the invention. It is then simpler to disperse the hormone in the solvent in which the polymer was previously dissolved. Thus, the second embodiment may use a single solvent such as dichloromethane. Commercially available dichloromethane is generally stabilized by ethanol (for example at 0.3% ethanol for pure dichloromethane for SDS synthesis). The invention may use this solvent either in the stabilized or unstabilized state.

Preferably, the material intended to form the matrix requires the use of poly(lactide-glycolide), polyactides, polylactic acids, poly(lactic-glycolic acids), polycaprolactones, polyvalerolactones, polyhydroxybutyrates, poly(hydroxybutyrate-valerate) as well as mixtures of these polymers. The polymers, in particular the polymers prepared from lactic acid and glycolic acid, or from lactide and glycolide cyclic dimers, generate, during their degradation, non toxic products which are metabolized by the body. The rate of degradation of these polymers is a factor which makes it possible to control the kinetics of release of the active ingredient, which may especially be varied from a few days to about one year.

The dispersion solvent is preferably evaporated under vacuum, advantageously completely. After taking up with the second solvent, the organic phase may be injected at a constant rate into the aqueous phase maintained with stirring. This aqueous phase preferably contains a dispersion stabilizer such as polyvinyl alcohol (PVA) (especially less than 5%, in particular between 0.5 and 2%), gelatine, or a surfactant such as "Tween 80." The organic solvent contained in the microspheres in suspension in the aqueous phase is preferably gradually evaporated by circulating compressed air (air bubbling) in the aqueous phase maintained with stirring. A few drops of an antifoaming agent such as a silicone emulsion may be advantageously added to the aqueous phase so as to avoid the formation of foam due to the bubbling of compressed air.

After evaporation of the solvent, the microspheres obtained may be recovered by filtration, washed with demineralized water and then optionally washed using a non solvent such as trichloro-trifluoro-ethane, heptane or petroleum ether. A highly free-flowing powder is thus obtained, especially with a particle size of less than 250 μm.

The process according to the invention makes it possible to incorporate the LHRH hormone or its analogues with a high yield using small quantities of organic solvents.

The process according to the invention makes it possible to preserve the substance in its original pulverulent state until the microspheres are formed in which it is homogeneously dispersed without aggregation, which, combined with the initial partition of the second solvent, makes it possible to substantially limit the substance losses which would otherwise occur by solubilization in the aqueous phase.

The encapsulation yield can be further improved by adjusting the temperature of the aqueous phase to between about 0° and 30° C. and in particular to between 10° and 25° C.

The process according to the invention is the first solvent evaporation process which makes it possible to obtain a high yield of encapsulation of the LHRH hormone and its analogues. The microspheres thus obtained are noteworthy especially in that the hormone is dispersed in a highly homogeneous manner and in its original pulverulent state, the process also making it possible to avoid aggregation of the particles. In addition, as specified above, the microspheres obtained have a low level of undesirable residual substances. Finally, the process makes it possible to obtain a wide range of microspheres incorporating the LHRH hormone or its analogues both from the point of view of the duration of release which may range from a few days to about 1 year, and from the point of view of their size, it being possible for the latter to exceed especially 50 to 60 microns, which sizes are not achieved by the techniques conventionally used for encapsulating water-soluble peptides in solid form, such as coacervation.

The subject of the invention is therefore also the microspheres capable of being obtained by the process according to the invention. The sizes of these microspheres may range from 1 to 250 microns, especially greater than 50 to 60 microns.

The subject of the present invention is also microspheres capable of being obtained by the process according to the invention and which are noteworthy in that the matrix constituting them comprises at least two types of polymer or copolymer, preferably two or three, which may especially differ in their nature or better still which may be of the same type but differ in one or more characteristics such as the ratio of constituent monomer units or their molecular masses. This makes it possible to vary the rate of release and to obtain a continuous release of long duration which may exceed especially 6 months. Other important advantages are related thereto, such as especially the polydispersity of the final mixture as well as a continuous release of active ingredient exhibiting a highly reduced prior induction phase, especially less than 5 to 10%, or even zero.

Preferably, the matrix comprises a mixture of two poly(DL-lactide-glycolide) polymers of different ratios ranging from 40–60 to 100–0. There may be mentioned, by way of example, a matrix comprising poly(DL-lactide-glycolide) 75–25 and poly (DL-lactide-glycolide) 50—50 and for example 360 mg and 40 mg respectively for a period of continuous release extending from D20 to about D180. The respective quantities of each of the types of polymers or copolymers is a factor which may, of course, also be varied.

The subject of the invention is also formulations comprising at least two types of microspheres according to the invention which differ in the composition of the matrices, for obtaining a continuous release of long duration, especially of the order of 8 months or more, and/or having a short or nonexistent latent time. The matrices may especially differ in their type or they may be of the same type but differ in their ratios of constituent monomer units and/or in their molecular masses. It is noteworthy that 8 months' of LHRH release can be matched or exceeded in vitro and in vivo using only two types of microspheres. It is especially possible to obtain, from two types of microspheres, a prolonged release matching or exceeding 8 months from the day of administration with a substantially continuous and close to zero order release profile.

Figure 2:
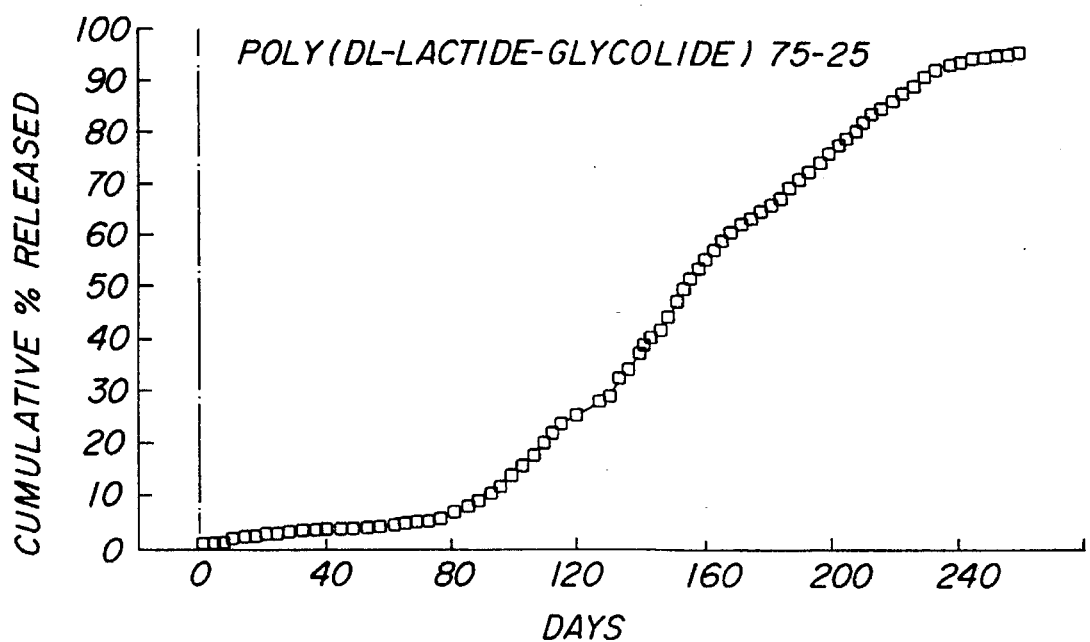
Figure 3:
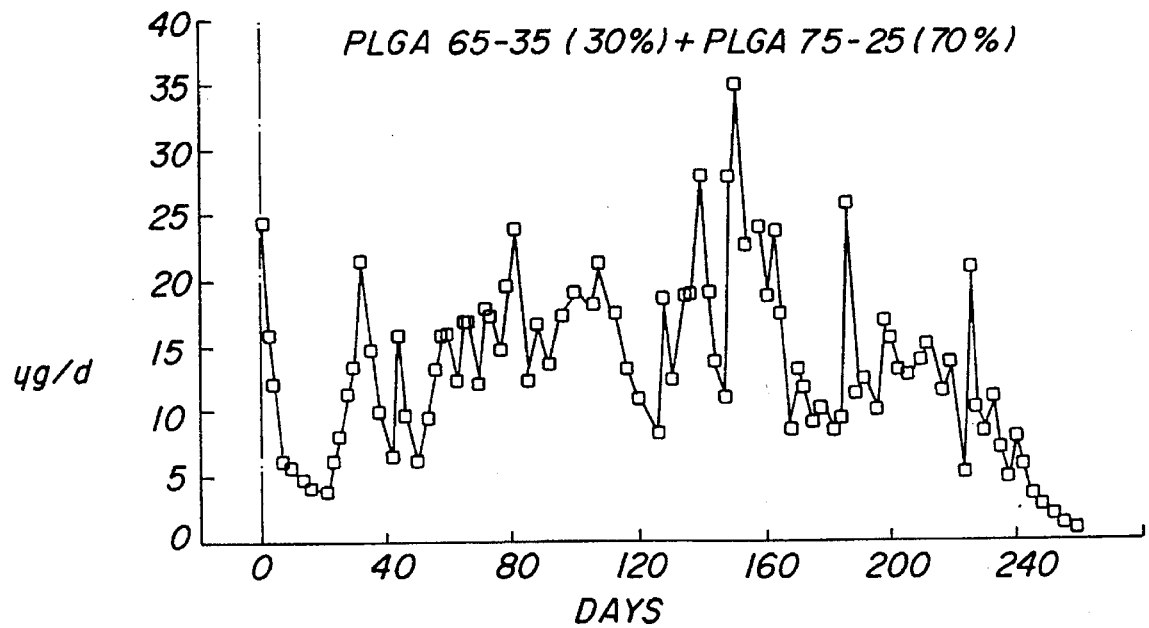
Figure 4:
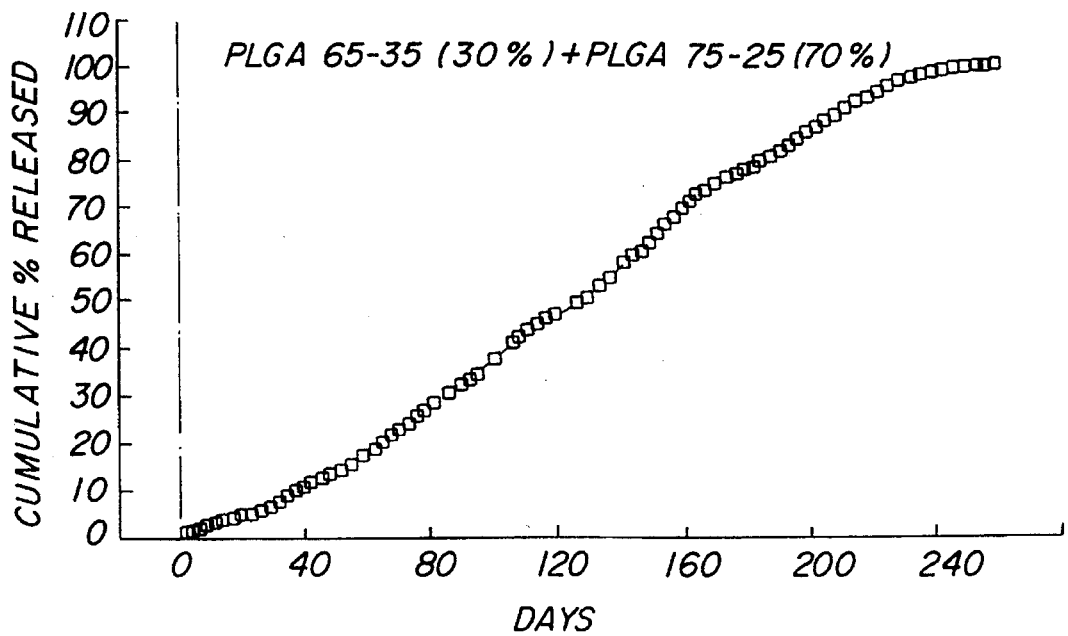
Figure 5:
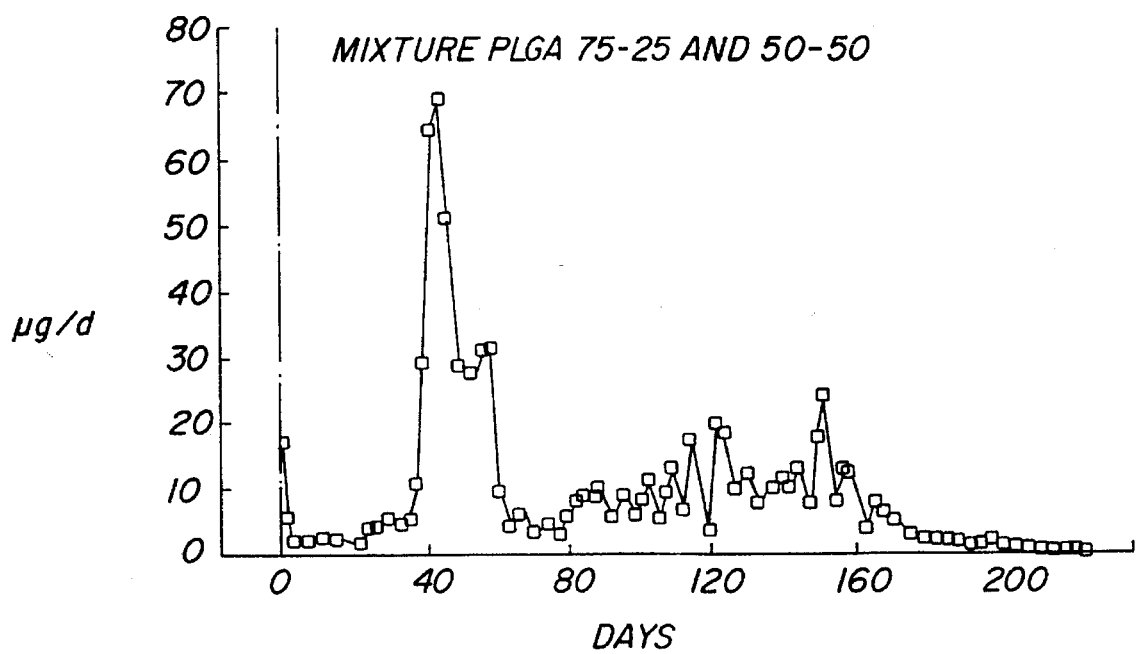

The invention will now be described in greater detail by means of embodiments of the process according to the invention for preparing microspheres incorporating a peptide [D-Trp$^6$]-LHRH and illustrating the kinetics of release of this peptide by means of the accompanying drawing showing:

in FIGS. 1 and 2, graphs showing the kinetics of release in vitro of [D-Trp$^6$]-LHRH in microspheres of poly(DL-lactide-glycolide) (=PLGA) 75–25, in µg/day and cumulative percentages respectively;

in FIGS. 3 and 4, graphs corresponding to those of FIGS. 1 and 2 for a mixture comprising 30% of microspheres containing PLGA 65–35 and 70% of microspheres containing PLGA 75–25;

in FIG. 5, a graph showing the kinetics of release in µg/day for microspheres whose matrix is a mixture of PLGA 75–25 and PLGA 50—50.

EXAMPLE 1

Method of Preparation, Encapsulation Yield

Encapsulation yield refers to the ratio of the quantity of active ingredient actually encapsulated to the total quantity of active ingredient used at the beginning of the process.

1. Preparation of the Microspheres

The organic phase, containing the polymer and the active ingredient, is prepared beforehand as follows: 400 mg of poly(DL-lactide-glycolide) 75–25, with an inherent viscosity of 0.59 dl/g, are dissolved in 3.5 g of tetrahydrofuran (THF). There are gradually added to this organic solution 39.6 mg of a freeze-dried [D-Trp$^6$]-LHRH hormone (trifluoroacetate) with stirring. The solvent is completely evaporated under vacuum and then the mass is dissolved in 2.4 g of dichloromethane with stirring. This [D-Trp$^6$]-LHRH hormone dispersion is injected into 500 ml of demineralized water containing 1% polyvinyl alcohol (PVA 8/88) at 19° C., with stirring. As soon as the injection is completed, three drops of antifoam (silicone emulsion) are added. The dichloromethane is then evaporated, still with stirring, by means of a bubbling of compressed air into the mixture. After evaporation of the solvent, the microspheres are harvested by filtration under vacuum, then they are washed with demineralized water in order to remove the residual PVA and a fraction of the silicone antifoam. The microspheres recovered are dried of their water on a filter and then washed with 1,1,2-trichloro-1,2,2-trifluoroethane in order to remove the residual antifoam. The microspheres are then recovered and stored at +4° C. The microspheres thus produced contain 8.1% [D-Trp$^6$]-LHRH (9% theoretical).

2. Encapsulation Yield

The abovementioned example refers to a peptide hormone salt of 10 amino acids, with a solubility of about 45 mg/ml in the continuous phase. Although the solubility of this peptide in water is high, high encapsulation yields are obtained.

An important parameter is the viscosity of the organic phase containing the polymer, the peptide dispersion and the solvent(s). The viscosity of the polymer/dichloromethane solution is measured at 19° C. by means of an Ostwald type viscometer and then the encapsulation trials are performed as described in Example 1 by varying the volume of dichloromethane and therefore the viscosity of the organic phase. In this case, a direct relationship is found between the viscosity and the encapsulation yield:

| Viscosity (Pa · s) | Encapsulation Yield (%) |
| --- | --- |
| 0.014 | 81 |
| 0.018 | 84 |
| 0.030 | 86 |
| 0.040 | 90 |

The encapsulation yield is determined from the extraction of the hormone from the microspheres produced and HPLC assay.

A yield of 90% may also be obtained with high peptide loads (15%), the load being defined as the ratio of the mass of peptide to the total quantity of polymer+peptide.

The microspheres produced under the conditions of optimal yield (viscosity>0.04 Pa.s) are <250 µm in size and are injectable after suspension in an appropriate aqueous vehicle.

A lowering of the temperature of the continuous aqueous phase makes it possible to further improve the encapsulation yield: if the mixture with a viscosity of 0.04 Pa.s used in Example 1 is injected into an aqueous phase at 13° C., the yield rises from 90 to 94%.

In order to form a peptide dispersion with a small particle size, other solvents or mixtures of solvents can be used such that the hormone remains in dispersed form without becoming solvated, for example chloroform, acetone, ethyl acetate and the like. The characteristics of these solvents, used pure or in the form of a mixture, are the fact that the peptide is dispersible therein with gentle stirring in order to obtain a particle size of a few microns, and the fact that the polymer used is soluble therein.

EXAMPLE 2

A simplification of the process may be provided if the organic phase/aqueous phase dispersion is accomplished directly without prior evaporation: 1 g of the poly(DL-lactide-glycolide) 75–25 mentioned in Example 1 is dissolved in 5.2 g of dichloromethane (commercial product SDS containing 0.3% of ethanol). 98.9 mg of a freeze-dried [D-Trp$^6$]-LHRH are dispersed in 0.53 g of dichloromethane (0.3% ethanol). The peptide dispersion is then mixed with the polymer solution with stirring, then this mixture is injected into 500 ml of demineralized water at 19° C. containing 1% PVA 8/88 with stirring. The rest of the process is identical to Example 1.

The encapsulation yield is 86%.

In a similar manner, the peptide is dispersed directly in the polymer-dichloromethane solution with gentle stirring: the procedure is then carried out as in Example 2.

Again in a similar manner, a freeze-dried [D-Trp$^6$, desGly 10, NH$_2$]-LHRH ethylamide is dispersed in the polymer solution and the dichloromethane, with gentle stirring. In an identical manner, the partition of the peptide into the aqueous phase remains low. Substantially similar yields are obtained.

Certain pairs of solvents for dispersing the peptide can be used as they are in the subsequent phase for dispersing the organic phase in the aqueous phase (dichloromethane/chloroform mixture). This therefore makes it possible to dispense with the dispersion solvent evaporation phase mentioned in Example 1 when the latter is immiscible or sparingly miscible with water (chloroform and the like).

The order of incorporation of the peptide or the polymer in the dispersion solvent may be interchanged while remaining in conformity with the invention.

EXAMPLE 3

Preparation of Microspheres from Poly(DL-lactide-glycolide) 65–35

2 g of poly (DL-lactide-glycolide) 65–35 with an inherent viscosity of 0.69 dl/g are dissolved in 8.9 g of THF. 198 mg of a freeze-dried [D-Trp$^6$]-LHRH are added to this solution with stirring. The solvent is evaporated under vacuum and with stirring, then the dry residue is dissolved in 11.8 g of dichloromethane with stirring. The suspension obtained is injected into 500 ml of demineralized water containing 1% of polyvinyl alcohol 8/88 at 20° C., with mechanical stirring (700 rpm). The rest of the process is identical to that of Example 1. Microspheres of <250 μm in size are obtained which form a free-flowing powder. The encapsulation yield is 86%.

EXAMPLE 4

Preparation of Microspheres from Poly(DL-lactide-glycolide) 75–25: Release of the Agonist [D-Trp$^6$]-LHRH from 80 to 240 Days The microspheres produced in Example 1, containing 8.1% [D-Trp$^6$]-LHRH, are used.

50 mg of microspheres are immersed in 5 ml of isotonic phosphate buffer pH 7.2, at 37° C. The supernatant is collected at regular intervals and it is replaced with 5 ml of buffer at 37° C. Each of the samples is then analysed by HPLC in order to determine the quantity of [D-Trp$^6$]-LHRH hormone released as a function of time.

The kinetics of release in vitro, compared with the kinetics in vivo, has made it possible to show their parallelism. The durations and profiles of release are especially identical in vitro and in vivo.

For the microspheres loaded at 8.1% [D-Trp$^6$]-LHRH, prepared from poly(DL-lactide-glycolide) 75–25, the following kinetics of release is obtained for 50 mg of microspheres (cf. FIGS. 1 and 2).

FIG. 1: After a small initial peak of release of the hormone, representing about 2% of the total quantity of hormone, the release in vitro is small up to about D80 corresponding to the induction phase, then the release increases gradually and stabilizes at about 20 μg/D up to the 220th day. The release then decreases and becomes zero after the 260th day.

FIG. 2: The cumulative fraction of hormone released in vitro shows that the release is close to zero order from D80 to D240.

EXAMPLE 5

Continuous Release of [D-Trp$^6$]-LHRH Hormone over 8 Months from a Mixture of Several Formulations If the formulations produced in Example 1 and in Example 3 are mixed, a system for the continuous release of the [D-Trp$^6$]-LHRH hormone over 8 months can thus be obtained.

The in vitro release trials performed by mixing 30% (on the basis of the quantity of peptide encapsulated in each of the formulations) of the poly(DL-lactide-glycolide) 65–35 formulation and 70% of the poly(DL-lactide-glycolide) 75–25 formulation under the same conditions as in Example 4, show that the two formulations indeed exhibit additivity and consequently complementarity: the PLGA 65–35 formulation releases the hormone from 0 to 85 days, then the PLGA 75–25 formulation releases the hormone from 80 to 240 days (FIG. 3). The release of hormone follows a kinetics close to 0 order up to D240 (FIG. 4).

EXAMPLE 6

Continuous Release of [D-Trp$^6$]-LHRH Hormone over 6 Months from the Mixture of 2 Polymers in a Single Formulation In order to obtain a continuous release of hormone over long periods (6 months or more), another method consists in mixing two, or even three, polymers with different characteristics inside the same formulation:

either two polymers having the same DL-lactide-glycolide ratio, but different molecular masses, such that the polydispersity of the final mixture is high, for example situated between 3.5 and 30, or two polymers having different DL-lactide-glycolide ratios such that the rate of degradation of either of these polymers is different, and allows the continuous release of the active ingredient without prior induction phase.

This type of mixture was prepared in the following example:

360 mg of poly(DL-lactide-glycolide) 75–25 (inherent viscosity 0.59 dl/g) and 40 mg of poly(DL-lactide-glycolide) 50—50 (inherent viscosity 0.44 dl/g) are dissolved in 3.5 g of THF. 16.7 mg of a freeze-dried [D-Trp$^6$]-LHRH (trifluoroacetate) are added to this solution with stirring. This solvent is then evaporated with stirring and the dry residue is then dissolved in 2.4 g of dichloromethane. The suspension obtained is injected into 500 ml of demineralized water containing 1% of polyvinyl alcohol 8/88 at 20° C., with mechanical stirring (700 rpm). The rest of the process is identical to that of Example 1. Microspheres of ≦250 μm in size are obtained which form a free-flowing powder. The encapsulation yield is 93%.

Kinetics of Release In Vitro 50 mg of the microspheres produced in Example 6 are immersed in 5 ml of phosphate buffer pH 7.2 at 37° C., and then the supernatant is removed at regular intervals in a manner identical to that of Example 4.

A clear shortening of the induction phase is observed (FIG. 5), passing from 80 days (cf. Example 4) to 20 days. This phase is followed by a period of continuous release of the hormone from D20 to D180.

The mixture of polymers with different characteristics therefore makes it possible to reduce the duration of the induction phase and permits the continuous release of the active ingredient over about 160 days in the present example.

We claim:

1. In a process for preparing microspheres comprised of LHRH hormone and analogues thereof dispersed in a water-insoluble polymer or copolymer matrix for the prolonged release of said hormone or its analogues, in which process the hormone is dispersed and the polymer or copolymer is dissolved in an organic solvent, the organic phase thus obtained is suspended in a continuous aqueous phase, the organic solvent is evaporated to form microspheres and the microspheres recovered, the improvement comprising using as said organic solvent, one or more organic solvents, wherein said organic solvent is slightly water-miscible, dissolves said polymer or copolymer and disperses therein said hormone or its analogues in the solid pulverant state by simply stirring wherein, said slightly water-miscible character of said solvent both allows said microsphere formation and decreases partition or loss of said hormone and its analogues by solubilization in said aqueous phase, thereby obtaining high yields of encapsulation of said hormone and analogues thereof in the solid pulverant state.

2. An improvement according to claim 1 wherein the organic solvent comprises a pair of organic solvents, a first solvent being slightly water-miscible and providing dissolution of said polymer or copolymer and a second organic solvent providing a homogenous suspension of LHRH hormones or analogues thereof in the solid pulverant state.

3. Process according to claim 1, wherein the organic solvent is chosen among the group consisting of dichloromethane, chloroform and mixtures thereof.

4. An improvement according to claim 2 wherein the second organic solvent is selected from tetrahydrofuran (THF), dioxane, acetone, acetonitrile, ethyl acetate, dichloromethane, chloroform, toluene, pyridine, benzyl alcohol, methyl ethyl ketone, mixtures thereof or chlorofluorocarbon-containing solvents.

5. An improvement according to claim 2 wherein first organic solvent is dichloromethane or chloroform.

6. An improvement according to claim 1 wherein the material intended to form the matrix is selected from poly(lactide-glycolide), polylactides, polylactic acids, poly(lactic-glycolic acid), polycaprolactones, polyvalerolactones, polyhydroxybutyrates, poly(hydroxybutyrate-valerate) and mixtures of these polymers.

7. An improvement according to claim 2, wherein that the hormone is dispersed in a first instance in the second solvent while the material intended to form the matrix is dissolved in the first solvent, then the two phases obtained are mixed in order to obtain the organic phase which is suspended in the aqueous phase.

8. An improvement according to claim 7 wherein the organic phase has a viscosity of between about 0.01 and 10 Pa.s.

9. An improvement according to claim 1 wherein the temperature of the aqueous phase is adjusted to between 0° and 30° C.

10. An improvement according to claim 1 wherein the organic solvent is evaporated by circulating compressed air in the aqueous phase maintaining the stirring.

11. An improvement according to claim 1 wherein as a few drops of an antifoaming agent, such as a silicone emulsion, are added to the aqueous phase.

12. An improvement according to claim 1 wherein after evaporation of the solvent, the microspheres obtained are recovered by filtration, washed with demineralized water and then optionally washed using a non-solvent.

13. Microspheres for the prolonged release of the LHRH hormone and of its analogues, which microspheres are obtained using the process according to claim 1.

14. Microspheres according to claim 13 wherein the matrix comprises at least two types of polymers or copolymers.

15. Microspheres according to claim 14 wherein the polymers or copolymers are of the same type but differ from each other in their ratios of constituent monomer units and/or in their molecular masses.

16. Microspheres according to claim 15 wherein the matrix comprises a mixture of two poly(DL-lactide-glycolide) polymers.

17. Microspheres according to claim 16 whose sizes are between about 1 and 250 microns.

18. Formulation for a release of long duration and/or having a short or nonexistent latent time, of the LHRH hormone and of its analogues, comprising at least two types of microspheres according to claim 13 differing by the composition of the matrices.

19. Formulation according to claim 18 wherein the matrices differ in their type, or are of the same type but differ in their ratios of constituent monomer units and/or in their molecular masses.

20. Formulation according to claim 19 wherein release is prolonged for a time equalling or exceeding 6 months.

* * * * *